US005487569A

United States Patent [19]
Silvis et al.

[11] Patent Number: 5,487,569
[45] Date of Patent: Jan. 30, 1996

[54] CONNECTOR FOR THREE OR MORE CAPILLARY TUBES

[75] Inventors: Paul H. Silvis, Boalsburg; Bradley R. Rightnour, Mingeville, both of Pa.

[73] Assignee: Restek Corporation, Bellefonte, Pa.

[21] Appl. No.: 321,973

[22] Filed: Oct. 12, 1994

[51] Int. Cl.$^6$ ........................................... F16L 35/00
[52] U.S. Cl. ................................ 285/24; 285/38; 285/61; 285/155; 285/342; 285/357; 285/911; 29/428
[58] Field of Search .................................. 285/24, 38, 61, 285/155, 342, 343, 357, 911; 29/428, 890.14

[56] References Cited

U.S. PATENT DOCUMENTS

| | | | |
|---|---|---|---|
| 4,529,230 | 7/1985 | Fatula | 285/911 X |
| 4,621,841 | 11/1986 | Wakefield | 285/911 X |
| 4,690,437 | 9/1987 | Anderson | 285/911 X |
| 4,997,213 | 3/1991 | Traner et al. | 285/155 |
| 5,234,235 | 8/1993 | Worden | 285/357 X |
| 5,288,113 | 2/1994 | Silvis et al. | 285/911 X |
| 5,303,553 | 4/1994 | Ollivaud et al. | 285/357 X |

*Primary Examiner*—Dave W. Arola
*Attorney, Agent, or Firm*—John F. A. Earley; John F. A. Earley, III

[57] ABSTRACT

An easily-assembled, heat resistant connector for releasably joining end portions of three capillary tubes for use in chromatography without interrupting flow or interfering with chromatographic results comprises a main body, and a glass insert which has first, second and third hollow legs that are connected together at a central portion, and a connector that connects each leg of the glass insert to a capillary tube. Each leg of the glass insert extends outwardly from the central portion towards an open end portion, and each leg has an inboard bore with a taper that receives and end portion of one of the capillary tubes. The taper is wider near the open end portion of the leg and narrower near the central portion. The connectors are mounted on the main body and a sealing ferrule is provided in each connector for making a seal between the capillary tubes and the legs of the glass insert. An adjusting screw in each connector provides for independently adjusting the pressure against each of the sealing ferrules to insure that an efficient seal is made between each capillary tube and a leg of the glass insert.

12 Claims, 4 Drawing Sheets

CONNECTOR FOR THREE OR MORE CAPILLARY TUBES

BACKGROUND OF THE INVENTION

1. Field of The Invention

The present invention is concerned with connectors for joining together the end portions of three or more capillary tubes for use in a gas chromatograph, for example, and is more particularly concerned with providing a connector between three or more capillary tubes which is easily assembled, has a number of leak-proof seals, and provides for an uninterrupted flow of fluids, such as a carrier gas, through the tubes.

2. Description of The Prior Art

Chromatographers and scientists of various disciplines have had a need to connect fused silica or stainless steel capillary tubes in end-to-end fashion with a connector that does not detract from chromatographic properties and does not interfere with the flow of fluids, such as a carrier gas, through the tubes. It is difficult to connect together the end portions of thin wall fused silica or stainless steel tubes with outside diameters ranging from 0.1 to 2.0 mm and inside diameters ranging from 0.01 to 1.6 mm because the connection may introduce unswept gaps that cause eddies and flow turbulence. Also, the connector may absorb active compounds which decrease the accuracy of the quantitative and qualitative analysis.

Restek Corporation U.S. Pat. No. 5,288,113 which issued on Feb. 22, 1994 to Paul H. Silvis, Bradley R. Rightnour, and Richard A. Morehead, addressed a number of these problems, and is incorporated herein by reference. However, Restek U.S. Pat. No. 5,288,113 was concerned with connecting together the end portions of two capillary tubes, whereas the present invention is concerned with connecting together the end portions of three or more capillary tubes.

SUMMARY OF THE INVENTION

Accordingly, it is an object of this invention to provide a connector for connecting together the end portions of three or more capillary tubes.

It is another object of the present invention to provide a capillary tube connector with secure seals that incorporate graphite ferrules.

It is another object to provide a connector which is free of dead spaces.

It is another object to provide a connector which does not detract from the inertness of the system.

It is another object to provide a connector which overcomes the unpredictability of connectors which utilize compressive forces solely at the tip of the tubes.

It is another object to provide a connector with seals that may be observed visually, so that the integrity of the seal is determined without requiring chromatographic testing.

It is another object to provide a connector which is reliable and easy to use.

It is another object to provide a connector that may be used at high temperatures, even temperatures exceeding 500° C.

It is another object to provide a connector which has independent adjustment screws for individually controlling the sealing pressure on each capillary tube.

It is another object to provide a connector for three or more tubes which is deactivated and inert toward active compounds.

It is another object to provide a connector for three or more tubes which does not rely on the polyamide coating on the tubes to create the seal.

It is another object to provide a connector for three or more tubes which has low mass and is easy to use.

It is another object to provide a connector for three or more tubes which splits the gas flow into two or more different paths. It is another object to provide a connector for three or more tubes which has connector legs that may be aligned independently of each other.

The ferrules used in this invention are preferably made of graphite available from many chromatography suppliers.

DETAILED DESCRIPTION OF TIME DRAWINGS

Turning now to the drawings, there is shown in Figs. 1–8 an easily-assembled, heat resistant connector 11 for releasably joining end portions of three capillary tubes 13, 14, and 15 for use in chromatography without interrupting fluid flow or interfering with chromatographic results.

Figure 1:
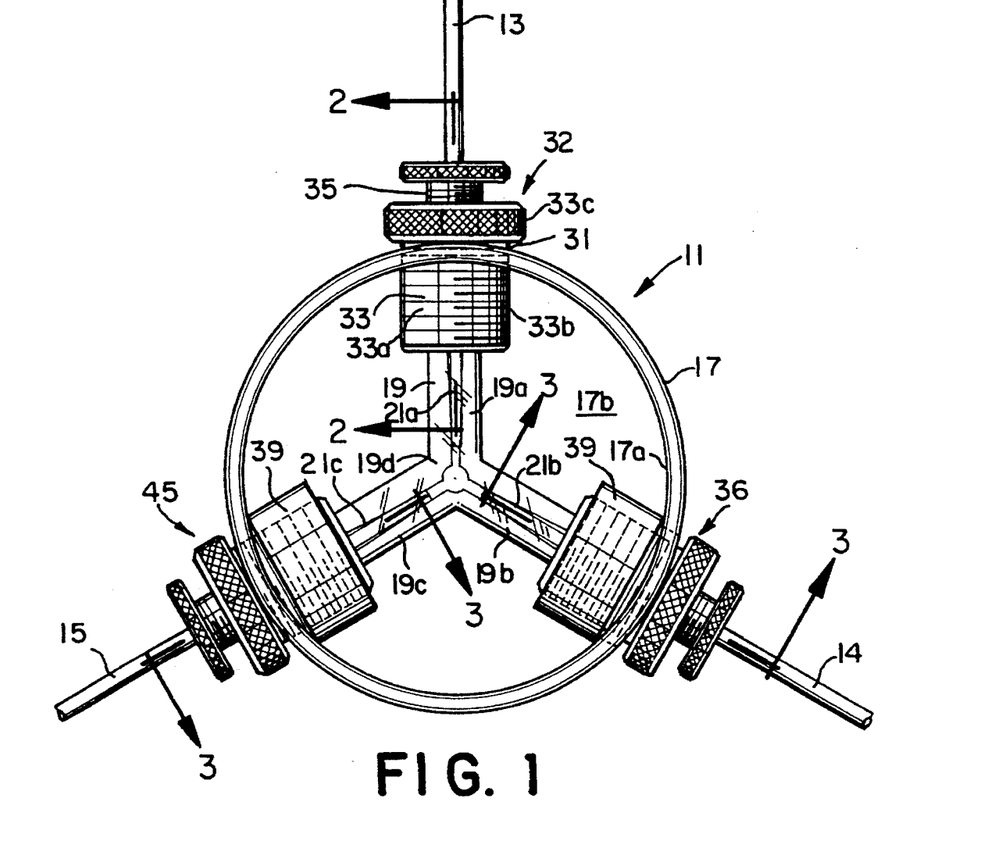
FIG. 1 is a view in top plan of a capillary tube connector constructed in accordance with this invention.

Tubes 13, 14 and 15 have a polyamide coating on the outer surfaces of the tubes.

The connector 11 includes a main body or ring 17 which is in the form of a ring having a cylindrical wall 17a and an interior space 17b inside the wall 17a.

A glass insert 19 is positioned in the interior space 17b of the main body 17 and is provided with a first or top hollow leg 19a, a second hollow leg 19b, and a third hollow leg 19c which are connected together by a central portion 19d. Each leg 19a, 19b, and 19c extends outwardly from the central portion 19d toward an open end portion.

Figure 2:
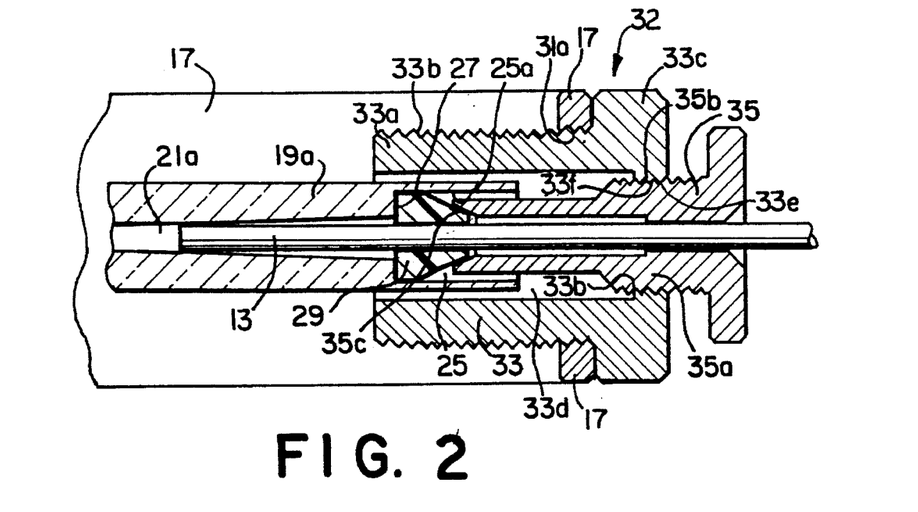
FIG. 2 is a view in section of the top leg of the connector taken as indicated by the lines and arrows 2—2 which appear in FIG. 1.
Figure 3:
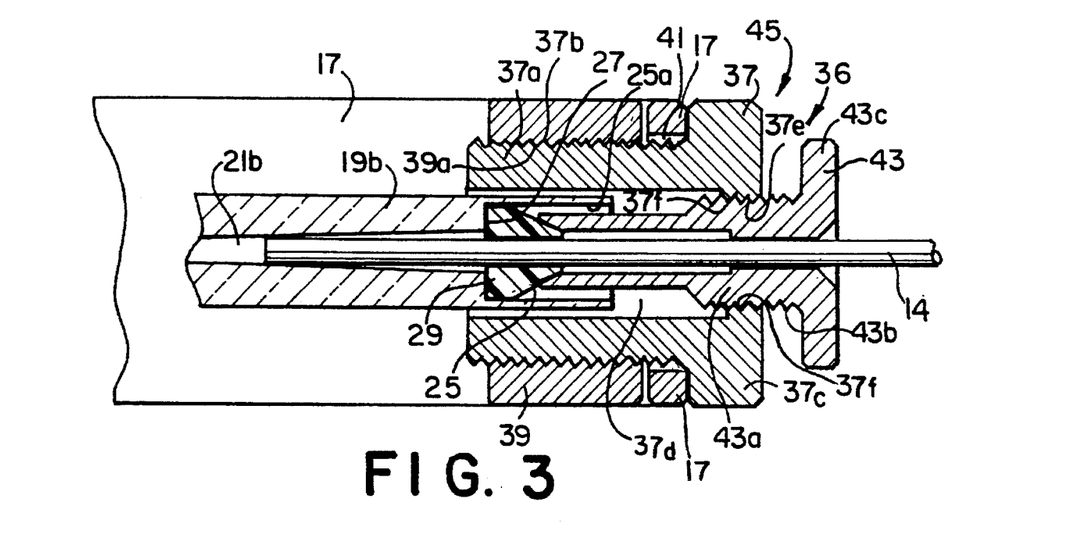
FIG. 3 is a view in section of the side legs of the connector taken as indicated by the lines and arrows 3—3 which appear in FIG. 1 at two places.
Figure 4:
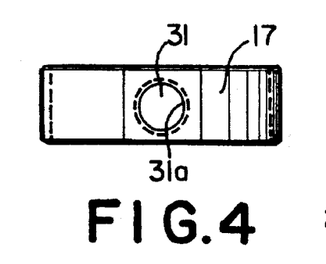
FIG. 4 is a view in side elevation of the top portion of the main body or ring.

Each leg 19a, 19b, 19c has an inboard bore 21a, 21b, and 21c with a taper that receives an end portion of one of the capillary tubes 13, 14, and 15. The taper is wider near the open end portions of the legs 19a, 19b, and 19c, and is narrower near the central portion 19d.

Each leg 19a, 19b, and 19c has an outboard bore or cup 25 which is larger in diameter than the diameter of the inboard bore 21a, 21b, and 21c. Each leg outboard bore 25 has an open outer end, and an inboard end with a stop shoulder 27. Each leg outboard bore 25 has an inner surface 25a.

A ferrule 29 is seated on the stop shoulder 27 in each leg 19a, 19b, and 19c, and each ferrule 29 has a bore for receiving the end portion of one of the capillary tubes 13, 14, and 15.

Each ferrule 29 is in the shape of a truncated cone with an inboard bottom base 29b (FIG. 6) that is wider than a outboard upper base 29c, and an inboard bottom portion 29d which has a cylindrical side surface 29e.

The main body 17 is provided with a top circular opening 31 (FIG. 4) that has inner threads 31a.

A first or top screw connector assembly 32 has a first screw support 33 with a cylindrical shaft 33a that has outer threads 33b, and is also provided with a knurled knob 33c at the outboard end of the shaft 33a for easily rotating the first screw support 33 into the inner threads 31a of the wall opening 31 of the main body 17.

An inboard bore 33d (FIG. 2) is formed in the first screw support 33, and the inboard bore 33d fits around the open end of the first leg 19a of the glass insert 19.

Top opening 31 of the main body 17 has inner threads 31a. Screw support 33 has outer threads 33b that screw into threads 31a of opening 31 in ring 17. An adjusting screw 35 is threaded into screw support 33 and has a shaft 35a with outer threads 35b that screw into inner threads 33f of first screw support 33.

Adjusting screw 35 is an independently operated adjusting screw for adjusting the pressure on ferrule 29, and has an inboard end with a frusto-conical end opening that mates with the cone surface 29f of the ferrule 29 for squeezing the ferrule 29 to form a seal with the first leg 19a in which it is seated. Adjusting screw 35 squeezes the bottom 29b of the ferrule 29 against the stop shoulder 27 of the first end portion 19a and squeezes the inboard bottom portion 29d of the ferrule 29 against the inner surface 25a of the leg outboard bore 25. The ferrule 29 forms four sealing areas: cone surface 29f against the frusto-conical end opening of screw 35, the inner surface of bore 29a against the outer surface of the end portion of the tube 13, bottom 29b against stop shoulder 27, and side surface 29e against the inner surface 25a of bore 25. Additionally, the end edges of the capillary tube 13 form a seal with the tapered portion of inboard bore 21a of connector leg 19a.

A second screw connector assembly 36 (FIG. 3) is provided and has a second screw support 37 having a cylindrical shaft 37a with outer threads 37b. A retaining ring 39 slidably fits around the second leg 19b of the glass insert 19, and the retaining ring 39 has inner threads 39a which receive the outer threads 37b of the second screw support 37.

A knurled knob 37c at the outer end of the shaft 37a is provided for easily rotating the second screw support 37 into the inner threads 39a of the retaining ring 39, whereby the second screw support 37 is screwed into the retaining ring 39 to connect the second capillary tube 14 to the second leg 19b of the glass insert 19.

Figure 5:
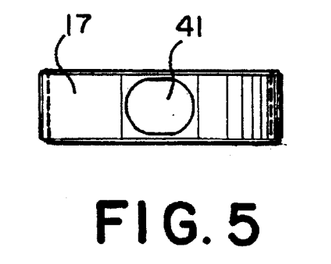
FIG. 5 is a view in side elevation of a side portion of the main body or ring that shows an elongated slot which accommodates a side leg of the connector.
Figure 6:
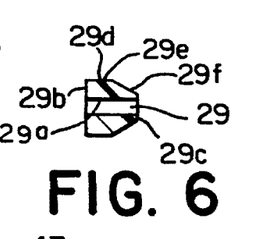
FIG. 6 is a view in section of a ferrule used in the invention.

An elongated slot 41 is provided in the wall 17a of the main body 17 to admit the shaft 37a of the second screw support 37 even though the second leg 19b of the connector 19 may not be precisely aligned with respect to the other legs 19a and 19c of the glass insert 19.

The second leg 19b has an inboard bore 21b with a taper that receives an end portion of second capillary tube 14.

There is an inboard bore 37d formed in the second screw support 37 which fits around the open end of the second leg 19b of the glass insert 19.

Also, an outboard bore 37f of the second screw support 37 is provided with inner threads 37e.

A second adjusting screw 43 has a shaft 43a with outer threads 43b that screw into the inner threads 37e of the outboard bore 37d of the second screw support 37.

A knurled knob 43c is provided on the outboard end of the second adjusting screw 43 for rotating the second screw 43 independently into the second screw support 37.

The knurled knob 37c of the second screw support 37 is wider than the elongated slot 41 in the wall 17a of the main body 17.

The connector 11 is also provided with a third screw support connector assembly 45 which is the same as the second screw support assembly 36.

Third screw support connector assembly 45 has a screw support 37 with a cylindrical shaft 37a with outer threads 37b that screw into threads 39a of retaining ring 39. Cylindrical shaft 37a slidably fits around the third leg 19c.

A knurled knob 37c at the outboard end of the shaft 37a is provided for easily rotating the third screw support 37 into the inner threads 39b of the retaining ring 39, whereby the screw support 37 is screwed into the retaining ring 39 to connect the third capillary tube 15 to the third leg 19c of the glass insert 19.

An elongated slot 41 is provided in the wall 17a of the main body 17 to admit the shaft 37a of the third screw support 47 even though the third leg 19c of connector 19 may not be precisely aligned with respect to the other legs 19a and 19b of the glass insert 19. The third leg 19c has an inboard bore 21c with a taper that receives an end portion 15 of third capillary tube 15.

An inboard bore 37d is formed in the third screw support 37 and fits around the open end of the third leg 19c of the glass insert 19.

An outboard bore is provided in third screw support 37 which has inner threads 37e.

A third adjusting screw 43 has a cylindrical shaft 43a with outer threads 43b that screw into the inner threads 37e of the outboard bore of the third screw support 37. A knurled knob 43c on the outboard end of the screw 43 is provided for rotating the third screw 43 independently into third screw support 37.

Knurled knob 37c of the third screw support 37 is wider than the elongated slot 41 in the wall 17a of the main body 17.

In operation, the method of assembly of second screw assembly 36 and third screw assembly 45 includes the steps of mounting the retainer rings 39 onto legs 19b and 19c of connector 19.

Then the end portion of the first capillary tube 13 is inserted through the first adjustment screw connector assembly 32 by inserting the end portion of the first capillary tube 13 through the first adjustment screw 35, through the first screw support 33, through the first ferrule 29 and into the tapered inner bore 21a of the first leg 19a of glass insert 19 to form a pressure seal between the tip of the capillary tube 13 and the inner surface of the inner bore 21a.

Then the first screw support 33 is screwed into the threads 31a of top opening 31 in main body 17 to hold leg 19a in outboard bore 33e, and the first adjustment screw 35 is rotated into the first screw support 33 to squeeze the first ferrule 29 against the end opening of screw 35, against the stop shoulder 27, against the inside surface 25a of outboard bore 25, and against the outer surface of tube 13 to form seals. The first adjustment screw 35 is independently rotated to adjust the pressure on the ferrule 29 in leg 19a.

To assemble the second screw assembly 36, the operation and method are as follows.

Retainer ring 39 has been inserted onto second leg 19b of connector 19. The end portion of capillary tube 14 is inserted through second adjusting screw 43, through second screw support 37, through a ferrule 29, and through the tapered inner bore 21b of second leg 19b of connector 19. The second screw support 37 is rotated into the retaining ring 39 to pull it tightly against the inside surface of main body 17.

The second screw support 37 extends through elongated slot 41 in wall 17a, and the second adjusting screw 43 is rotated into the second screw support 37 and onto the second ferrule 29. The end opening of screw shaft 43a squeezes the ferrule against the stop shoulder 27 of leg 19b, against the walls of the outboard bore 25 of the second leg 19b, and against tube 14, to form seals, and to form a seal between the end portion of the capillary tube 14 and the second leg 19b of the connector 19.

Then the end portion of the third capillary tube 15 is inserted through third screw assembly 45, through the adjustment screw 43, through the adjustment screw support 37, through the ferrule 29 and into the inner bore of leg 15 to form a seal against the tapered inside surface of the inner bore of the third leg 19c of the glass insert 19.

The third adjusting screw support 37 of third screw connector assembly 45 is screwed into the retaining ring 39 to bring the retaining ring 39 and the adjusting screw support 37 uptight against the inside edges of the elongated slot 41 in wall 17a.

The adjusting screw 43 in assembly 45 is rotated independently against the third ferrule 29 to squeeze the ferrule against the end opening 35c of screw 43. Screw 43 squeezes the ferrule against stop shoulder 27 of the third leg 19c of the glass insert 19, and squeezes the wall 29e of the ferrule 29 against the interior surface of the outboard bore 25 of the third leg 19c, and against the outer surface of tube 15, to form seals.

In operation and use of the invention, a fluid is passed through the first capillary tube 13 into the connector 11 through leg 19a.

The fluid is split in the connector 19 into two portions. A first portion is passed out of the connector 19 through second leg 19b and second capillary tube 14. The other portion of the fluid is passed out of the connector 19 through the third leg 19c of the connector 19 and the third capillary tube 15.

Figure 7:
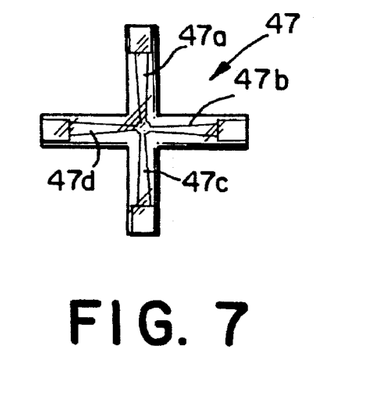
FIG. 7 shows a view in top plan of another embodiment of a glass insert having four legs.

FIG. 7 shows a glass insert 47 which has four legs 47a, 47b, 47c, and 47d, wherein a test fluid may be inserted through leg 47a and split into three exit paths through legs 47b, 47c, and 47d.

Figure 8:
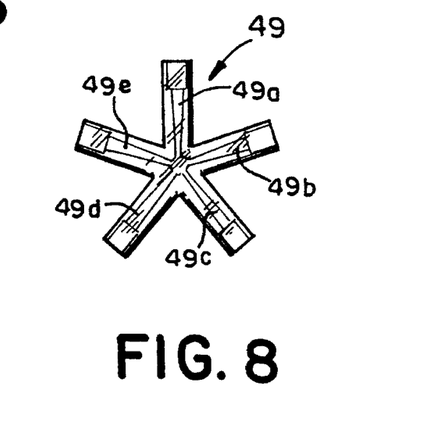
Fig. 8 is a view in top plan of another embodiment of glass insert which has five legs.

FIG. 8 shows a glass insert 49 which has five legs 49a, 49b, 49c, 49d, and 49e. Here, the test fluid may be inserted into input leg 29a and split four ways and may exit through legs 49b, 49c, 49d, and 49e.

Turning now to the presently preferred embodiment of the connector 51 constructed in accordance with the invention and shown in FIGS. 9–13, there is shown a main body or ring 53, a glass insert 19 which has a first hollow leg 19a, a second hollow leg 19b, and a third hollow leg 19c that are connected together at a central portion 19d. Each leg 19a–19c extends outwardly from the central portion 19d towards an open end portion of the legs.

Figure 9:
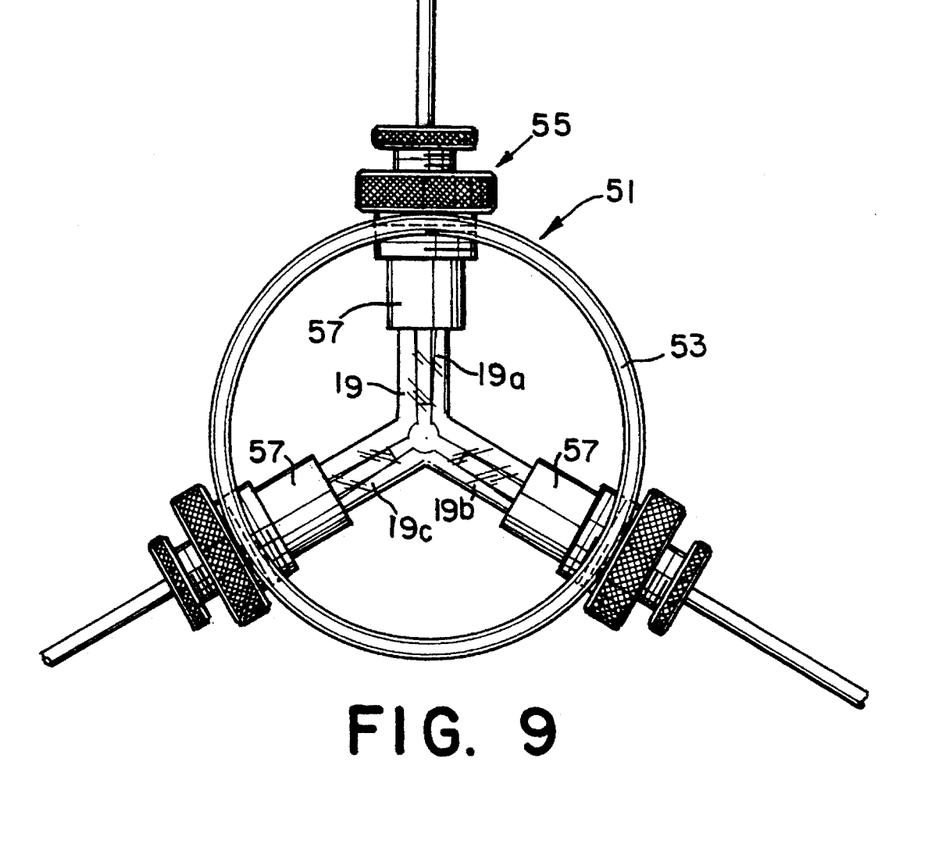
Fig. 9 is a view in top plan of a presently preferred capillary tube connector constructed in accordance with this invention.

Each leg 19a–19c has an inboard bore with a taper that receives an end portion of one of the capillary tubes 13–15, and the taper is wider near the open end portion of the legs 19a–19c and is narrower near the central portion 19d of the glass insert 19.

A connector assembly 57 is mounted on the main body 53 in the same manner as first screw connector assembly 32 is mounted in main body 17 which is shown in FIG. 2, with the only difference being that a screw support 57 is substituted for the screw support 33.

Figure 10:
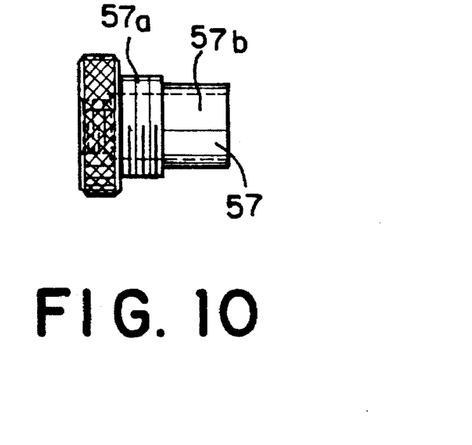
Fig. 10 is a view in side elevation of a screw support of the connector of FIG. 9.
Figure 11:
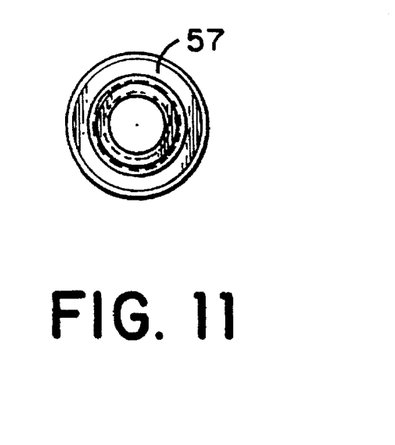
Fig. 11 is a view in top plan of the screw support of Fig 10.
Figure 12:
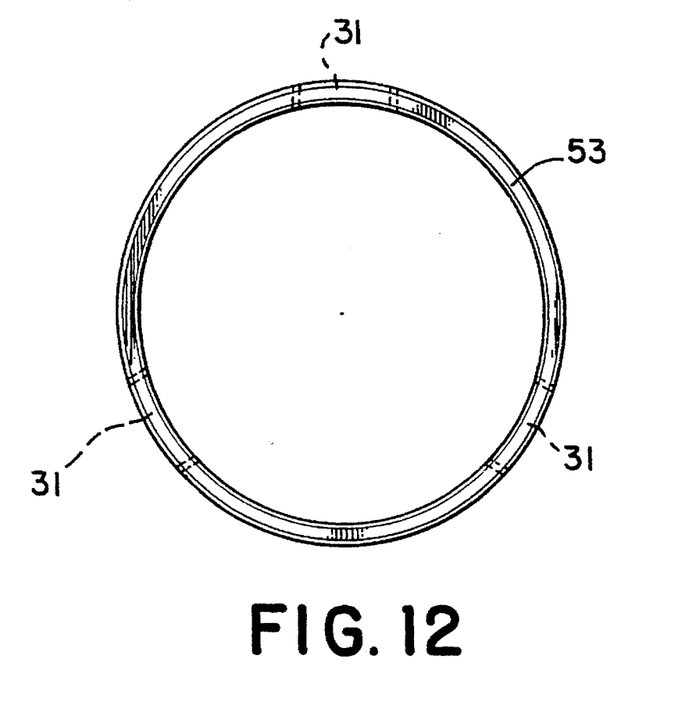
Fig. 12 is a view in top plan of the ring of Fig, 9.
Figure 13:
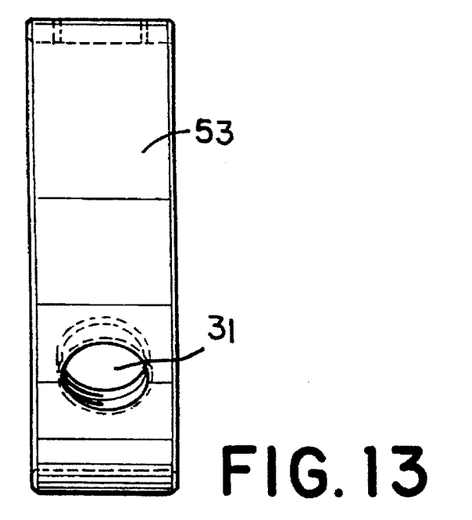
Fig. 13 is a view in side elevation of the ring of FIG. 12.

Screw support 57 differs from screw support 33 only in that screw threads 57a do not extend as far down screw cylindrical shaft 57b since screw support 57 needs only to be threaded into inner threads 31a in openings 31 in ring 53, there being three openings 31 in ring 53 as compared to the one opening 31 in ring 17.

Since retaining rings 39 are not used in connector 51 of FIG. 9, there is no need to extend the threads 57b down to the end of the cylindrical shaft 57b.

Connector 51, as in connector assembly 32, is provided with a ferrule 29 for making seals between the capillary tubes 13–15 and the legs 19a–19c of the glass insert 19.

Other than the changes described above, connector 51 is provided with the same adjusting means as first screw connector assembly 32, including adjusting screw 35.

We claim:

1. An easily-assembled, heat resistant connector (11) for releasably joining end portions of three capillary tubes (13, 14, 15) for use in chromatography without interrupting fluid flow or interfering with chromatographic results, comprising a main body (17) having a cylindrical wall (17a) and an interior space (17b) inside the wall (17a), a glass insert (19) having first (19a), second (19b) and third (19c) hollow legs which are connected together at a central portion (19d) and are spread apart, each leg (19a, 19b, 19c) extending outwardly from the central portion (19d) towards an open end portion, each leg (19a, 19b, 19c) having an inboard bore (21a, 21b, 21c) with a taper that receives an end portion of one of the capillary tubes (13, 14, 15), said taper being wider near the open end portion of the leg (19a, 19b, 19c) and narrower near the central portion (19d), each leg (19a, 19b, 19c) having an outboard bore (25) which is larger in diameter than the diameter of the inboard bore (21a, 21b, 21c), each leg outboard bore (25) having an open outer end and an inboard end with a stop shoulder (27), each leg outboard bore (25) having an inner surface (25a), a ferrule (29) seated on the stop shoulder (27) of each leg (19a, 19b, 19c)

each ferrule (29) having a bore for receiving the end portion of one of the capillary tubes (13, 14, 15), each ferrule (29) being in the shape of a truncated cone with an inboard bottom base (29b) that is wider than its outboard top base (29c), and an inboard bottom portion (29d) with a cylindrical side surface, a number of openings in the main body, said openings being spaced apart around the wall of the main body, screw connector assembly means mounted on the main body in said openings and connected to the glass insert legs for holding the glass insert in place, with a first screw connector assembly (32) for controlling sealing pressure including a first screw support (33) having a hollow shaft (33a) with outer threads (33b), a knurled knob (33c) at the outboard end of the shaft (33a) for easily rotating the first screw support (33), an inboard bore (33d) formed in the first screw support (33), said screw support inboard bore (33d) fitting around the open end of the first leg (19a) of the glass insert (19), an outboard bore (33e) of the first screw support (33), said first screw support outboard bore (33e) having inner threads (33f), a ferrule seated in the cup at the open end portion of the legs, and an adjusting screw (35) having outer threads (35b) for screwing into the inner threads (33f) of the outboard bore (33e) of the first screw support (33) and squeezing the ferrule to form seals between the ferrule and the capillary tube and between the ferrule and the legs of the glass insert.

2. The connector of claim 1, said adjusting screw (35) having an inboard end with a frusto-conical end opening that mates with the cone surface (33f) of the ferrule (29) for squeezing the ferrule (29) to form said seal between the bottom base (29b) of the ferrule (29) and the stop shoulder (27), and to form a seal between the inboard bottom portion (29d) of the ferrule (29) and the inner surface of the leg outboard bore (25), and to form a seal between the ferrule bore and the tube (13).

3. The connector of claim 1 including, a second screw connector assembly (36) for controlling sealing pressure including a second screw support (37) having a shaft (37a) with outer threads (37b), a retaining ring (39) which slidably fits around the second leg (19b) and screws onto the shaft of the second screw support for clamping the second screw support and said retaining ring in position against the main body, said retaining ring being located in the interior space (17b) inside the main body, an inner opening in the retaining ring (39) having inner threads (39a) which receive the outer threads (37b) of the second screw support (37) for retaining the screw support (37) and said retaining ring against the main body (17), a knurled knob (37c) at the outboard end of the shaft (37a) of second screw support (37) for easily rotating the second screw support (37) into the inner threads (39a) of the retaining ring (39), whereby said second screw support (37) is screwed into said retaining ring (39) to connect the second capillary tube (14) to the second leg (19b) of the glass insert (19), an elongated slot (41) in the wall (17a) of the main body (17) to admit the shaft (37a) of the second screw support (37) even though the second leg (19b) may not be precisely aligned with respect to the other legs (19a, 19c) of the glass insert (19), said second leg (19b) having an inboard bore (21b) with a taper that receives an end portion of second capillary tube (14), an inboard bore (37d) formed in the second screw support (37), said second screw support inboard bore (37d) fitting around the open end of the second leg (19b) of the glass insert (19), an outboard bore of the second screw support (37), said second screw support outboard bore having inner threads (37e), a second adjusting screw (43) having outer threads (43b) for threading into the inner threads (37e) of the outboard bore (37d) of the second screw support (37), and a knurled knob (43c) on the outboard end of the second screw (43) for rotating the second screw (43) into the second screw support (37) to apply a desired pressure onto the ferrule (29), said knurled knob (43c) of the second screw support (37) being wider than the elongated slot (41) in the wall (17a) of the main body (17).

4. The connector of claim 3 including, a third independently operated screw connector assembly (45) for controlling sealing pressure including a third screw support having a shaft with outer threads, a retaining ring positioned in the interior space inside the main body and which slidably fits around the third leg (19c), an inner opening in the retaining ring having inner threads which receive the outer threads of the third screw support, a knurled knob at the outboard end of the shaft for easily rotating the third screw support into the inner threads of the retaining ring, whereby said third screw support is screwed into said retaining ring for clamping the third screw support and retaining ring against the main body and to connect the third capillary tube (15) to the third leg (19c) of the glass insert (19), an elongated slot in the wall (17a) of the main body (17) to admit the shaft of the third screw support even though the third leg (19c) of the glass insert may not be precisely aligned with respect to the other legs (19a, 19b) of the glass insert (19), said third leg (19c) having an inboard bore with a taper that receives an end portion of third capillary tube (15), an inboard bore formed in the third screw support, said third screw support inboard bore fitting around the open end of the third leg (19c) of the glass insert (19), an outboard bore of the third screw support, said third screw support outboard bore having inner threads, a third adjusting screw having outer threads for screwing into the inner threads of the outboard bore of the third screw support, a knurled knob on the outboard end of the third screw for rotating the third screw into the third screw support, and a knurled knob of the third screw support which is wider than the elongated slot in the wall (17a) of the main body (17).

5. The connector of claim 1,
   the top opening (31) in wall (17a) of the main body (17) having a circular circumference,
   and inner threads of the circular circumference which receive the threads of the first screw support.

6. An easily-assembled, heat resistant connector for releasable joining end portions of three capillary tubes for use in chromatography without interrupting fluid flow or interfering with chromatographic results, comprising
   a main body having a cylindrical wall and an interior space inside the wall,
   a glass insert having first, second and third hollow legs which are spread apart and which are connected together at a central portion,
   each leg extending outwardly from the central portion toward an open end portion,
   each leg having an inboard bore with a taper that receives an end portion of one of the capillary tubes,
   said taper being wider near the open end portion of the leg and narrower near the central portion (19d),
   each leg (19a, 19b, 19c) having an outboard bore which is larger in diameter than the diameter of the inboard bore,
   each leg outboard bore having an open outer end and an inboard end with a stop shoulder,
   each leg outboard bore having an inner surface,
   a ferrule seated on the stop shoulder of each leg (19a, 19b, 19c)
   each ferrule having a bore for receiving the end portion of one of the capillary tubes,
   each ferrule being in the shape of a truncated cone with an inboard bottom base that is wider than its outboard upper base, and an inboard bottom portion with a cylindrical side surface,
   a number of openings in the wall of the main body,
   said openings being spread apart around the wall of the main body,
   screw connector assembly means mounted in said wall openings and connected to the glass insert legs for holding the glass insert in place, with
   a first screw support having a shaft with outer threads,
   a knurled knob at the outboard end of the shaft for easily rotating the first screw support,
   an inboard bore formed in the first screw support,
   said screw support inboard bore fitting around the open end of the first leg of the glass insert to hold the first leg in place,
   an outboard bore of the first screw support,
   said first screw support outboard bore having inner threads,
   and an adjusting screw having outer threads adapted to screw into the inner threads of the outboard bore of the first screw support,
   said adjusting screw having an inboard end with a frusto-conical end opening that mates with the cone of the ferrule for squeezing the ferrule to form a seal between the ferrule and the first leg and between the ferrule and the first tube,
   a second screw support having a shaft with outer threads positioned through one of the openings in the wall of the main body,
   a retaining ring which slidably fits around the second leg and screws onto the shaft of the second screw support and retaining ring for clamping the second screw support against the main body,
   an inner opening in the retaining ring having inner threads which receive the outer threads of the second screw support,
   a knurled knob at the outboard end of the shaft for easily rotating the second screw support,
   whereby said second screw support is screwed into said retaining ring to clamp the second screw support to the main body and to connect the second capillary tube to the second leg of the glass insert,
   one of said openings in the main body being an elongated slot in the wall of the main body to admit the shaft of the second screw support even though the second leg may not be precisely aligned with respect to the other legs of the glass insert,
   said second leg having an inboard bore with a taper that receives an end portion of second capillary tube,
   an inboard bore formed in the second screw support,
   said second screw support inboard bore fitting around the open end of the second leg of the glass insert,
   an outboard bore of the second screw support,
   said second screw support outboard bore having inner threads,
   a second adjusting screw having outer threads adapted to screw into the inner threads of the outboard bore of the second screw support, and
   a knurled knob on the outboard end of the second screw for rotating the second screw into the second screw support,
   said knurled knob of the second screw support being wider than the elongated slot in the wall of the main body,
   a third screw support having a shaft with outer threads,
   a retaining ring which slidably fits around the third leg,
   an inner opening in the retaining ring having inner threads which receive the outer threads of the third screw support,
   a knurled knob at the outboard end of the shaft for easily rotating the third screw support into the inner threads of the retaining ring,
   whereby said third screw support is screwed into said retaining ring through one of said openings in said main body clamp the main body between said screw support and the retaining ring to connect the third capillary tube to the third leg of the glass insert,
   one of said openings in the main body being an elongated slot in the wall of the main body to admit the shaft of the third screw support even though the third leg may not be precisely aligned with respect to the other legs of the glass insert,
   said third leg having an inboard bore with a taper that receives an end portion of third capillary tube,
   an inboard bore formed in the third screw support,
   said third screw support inboard bore fitting around the open end of the third leg of the glass insert,
   an outboard bore of the third screw support,
   said third screw support outboard bore having inner threads,
   a third adjusting screw having outer threads adapted to screw into the inner threads of the outboard bore of the third screw support, and
   a knurled knob on the outboard end of the third screw for rotating the third screw into the third screw support, and said knurled knob of the third screw support being wider than the elongated slot in the wall of the main body.

7. An easily-assembled, heat resistant connector for releasable joining end portions of three capillary tubes for use in chromatography without interrupting fluid flow or interfering with chromatographic results, comprising a main body having a wall and an interior space inside the wall, a glass insert having first, second and third hollow legs which are spaced apart and are connected together at a central portion, each leg extending outwardly from the central portion toward an open end portion, each leg having an inboard bore that receives an end portion of one of the capillary tubes, each leg having an outboard bore which is larger in diameter than the diameter of the inboard bore, each leg outboard bore having an open outer end and an inboard end with a stop shoulder, each leg outboard bore having an inner surface, a ferrule seated on the stop shoulder of each leg, each ferrule having a bore for receiving the end portion of one of the capillary tubes, a number of openings in the wall of the main body, said openings being spaced apart around the wall, screw connector assembly means mounted on the main body in said openings and connected to the glass insert to hold the glass insert in place and to connect each leg to a capillary tube, a first screw support having a hollow cylindrical shaft, a knurled knob at the outboard end of the shaft for easily rotating the first screw support, an inboard bore formed in the first screw support, said screw support inboard bore fitting around the open end of the first leg of the glass insert, and an adjusting screw adjustably mounted on the first screw support for controlling sealing pressure on the ferrules and on the tube.

8. An easily-assembled, heat resistant connector for releasable joining end portions of three capillary tubes for use in chromatography without interrupting fluid flow or interfering with chromatographic results, comprising a main body, a glass insert having first, second and third hollow legs that are spread apart and are connected together at a central portion, each leg extending outwardly from the central portion towards an open end portion which has a cup formed therein, each leg having an inboard bore with a taper that receives an end portion of one of the capillary tubes, said taper being wider near the open end portion of the leg and narrower near the central portion, connector assembly means mounted on the main body for connecting capillary tubes to the legs of the glass insert, sealing means in the connector assembly means for making a seal between the sealing means and the capillary tubes and a seal between the sealing means and the legs of the glass insert, and adjusting means in the connector assembly means for adjusting pressure against the sealing means.

9. The connector of claim 8, wherein the main body has a cylindrical wall and an interior space inside said wall, said connector assembly means includes a circular opening in the wall of the main body, inner threads in the circular opening, a screw support having a hollow shaft with outer threads for threading into the inner threads of the circular opening, an inboard bore formed in the screw support, said inboard bore of the screw support fitting around the open end portion of a leg of the glass insert, an outboard bore formed in the screw support, said outboard bore having inner threads, said sealing means comprising a ferrule seated in the cup at the open end portion of the leg of the glass insert, and an adjusting screw which screws into the screw support and squeezes the ferrule to form seals between the ferrule and the leg of the glass insert and between the ferrule and a capillary tube in the ferrule.

10. A method of sealingly connecting end portions of three capillary tubes together, comprising the steps of providing an easily-assembled, heat-resistant capillary tube connector for releasably joining end portions of three capillary tubes in end-to-end fashion for use in chromatography without interrupting fluid flow or interfering with chromatographic results, comprising a main body having a cylindrical wall and an interior space inside the wall, a glass insert having a first, second and third hollow legs which are spread apart and which are connected together at a central portion, each leg extending outwardly from the central portion toward an open end portion, each leg having an inboard bore with a taper that receives an end portion of one of the capillary tubes, said taper being wider near the open end portion of the leg and narrower near the central portion, each leg having an outboard bore which is larger in diameter than the diameter of the inboard bore, each leg outboard bore having an open outer end and an inboard end with a stop shoulder, each leg outboard bore having an inner surface, a ferrule seated on the stop shoulder of each leg, each ferrule having a bore for receiving the end portion of one of the capillary tubes, each ferrule being in the shape of a truncated cone with an inboard bottom that is wider than its outboard top, and an inboard bottom portion with a cylindrical side surface, a number of openings in the main body, said openings being spaced apart around the wall of the main opening, screw connector assembly means mounted on the main body in said openings and connected to the glass insert legs for holding the glass insert in place, with a circular opening in the wall of the main body, inner threads on the circular opening of the wall opening, a first screw support having a shaft with outer threads, a knurled knob at the outboard end of the shaft for easily rotating the first screw support into the inner threads of the wall opening of the main body, an inboard bore formed in the first screw support, said screw support inboard bore fitting around the open end of the first leg of the glass insert, an outboard bore of the first screw support, said first screw support outboard bore having inner threads, and an adjusting screw having outer threads which screw into the inner threads of the outboard bore of the first screw support, said adjusting screw having an inboard end with an end opening in the shape of a cone that mates with the cone of the ferrule for squeezing the ferrule to form a seal between the ferrule and the first leg, and between the ferrule and a capillary tube in the bore of the ferrule, a second screw support assembly means mounted in an opening in the main body for connecting a second capillary tube to the second leg of the glass insert, a retaining ring which slidably fits around the second leg of the glass insert, an inner opening in the retaining ring having inner threads which receive the outer threads of the second screw support, a knurled knob at the outboard end of the shaft of the second screw support for easily rotating the second screw support into the inner threads of the retaining ring and clamping the second screw support and retaining ring to the main body, whereby said second screw support is screwed into said retaining ring to connect the second capillary tube to the second leg of the glass insert, one of said openings in the main body being an elongated slot in the wall of the main body to admit the shaft of the second screw support even though the second leg of the glass insert may not be precisely aligned with respect to the other legs of the glass insert, said second leg having an inboard bore with a taper that receives an end portion of the second capillary tube, an inboard bore formed in the second screw support, said second screw support inboard bore fitting around the open end of the second leg of the glass insert, an outboard bore of the second screw support, said second screw support outboard bore having inner threads, a second adjusting screw having outer threads adapted to screw into the inner threads of the outboard bore of the second screw support, and a knurled knob on the outboard end of the second screw for rotating the second screw into the second screw support, a third screw support assembly means mounted in an opening in the main body for connecting a third capillary tube to the third leg of the glass insert, a retaining ring which slidably fits around the third leg, an inner opening in the retaining ring having inner threads that receive the outer threads of the third screw support, a knurled knob at the outboard end of the shaft of the third screw support for easily rotating the third screw support into the inner threads of the retaining ring, whereby said third screw support is screwed into said retaining ring to clamp them to the main body and connect the third capillary tube to the third leg of the glass insert, an elongated slot in the wall of the main body to admit the shaft of the third screw support even though the third leg of the glass insert may not be precisely aligned with respect to the other legs of the glass insert, said third leg having an inboard bore with a taper that receives an end portion of the third capillary tube, an inboard bore formed in the third screw support, said third screw support inboard bore fitting around the open end of the third leg of the glass insert, an outboard bore of the third screw support, said third screw support outboard bore having inner threads, a third adjusting screw having outer threads adapted to screw into the inner threads of the outboard bore of the third screw support, a knurled knob on the outboard end of the third screw for rotating the third screw into the third screw support, and said knurled knob of the third screw-support being wider than the elongated slot in the wall of the main body, the method further comprising the steps of:

placing the glass insert inside the main body, mounting a retainer ring onto a second leg of the glass insert;

mounting a retaining ring onto third leg of the glass insert, inserting the end portion of the first capillary tube through the first adjustment screw, through the first screw support, through the first ferrule and into the tapered inner bore of the first leg of the glass insert to form a pressure seal between the tip of the capillary tube and the inner surface of the tapered inner bore, rotating the first screw support into the threads of circular top opening in the main body to hold the top leg in the outboard bore of the screw support, rotating the first adjustment screw into the first screw support so that the end opening of the screw squeezes the first ferrule against the stop shoulder and against the inside surface of inboard bore of the first screw support and against the capillary tube, rotating the first adjustment screw to adjust the pressure on the first ferrule, inserting the second screw support through the elongated slot into the interior space of the main body, inserting the end portion of the second capillary tube through the second adjusting screw, through the second screw support, through the second ferrule and through the tapered inner bore of second leg of the glass insert, rotating the second adjusting screw into the second screw support and onto the second ferrule to squeeze it against the stop shoulder and the side walls of the outboard bore of the second leg to form a seal between the ferrule and the end portion of capillary tube and between the ferrule and the second leg of the connector, inserting the end portion of third capillary tube through the third adjustment screw, through the third adjusting screw support, through the third ferrule and into the inner bore of the third leg to form a seal against the tapered inside surface of the inner bore of the third leg of glass insert, rotating the third adjusting screw support into the third retaining ring to bring the retaining ring and the third adjusting screw support uptight against the edges of the elongated slot and clamp the retaining ring and the third adjusting screw support to the main body, rotating the third adjusting screw independently against the third ferrule to squeeze the ferrule to form a seal with the third leg of the glass insert and to form a seal with the tube, passing a fluid through the first capillary tube into the connector through the top leg of the glass insert, splitting the fluid in the connector into two portions, passing one portion out of the connector through the second leg of the glass insert and second capillary tube, and passing the other portion of the fluid from the connector through the third leg of the glass insert and the third capillary tube.

11. An easily-assembled, heat resistant connector for releasably joining end portions of at least three capillary tubes, comprising a glass insert with at least three hollow legs which are spread apart from a central portion, a main body having a cylindrical wall and an interior space inside the wall, holding means mounted on the main body and connected to each leg for holding the glass insert in place in said interior space, a ferrule mounted in each leg of the glass insert, each ferrule having a bore for receiving an end portion of a capillary tube, and individual adjusting means mounted in the holding means for individually squeezing each ferrule to form a seal between the ferrule and its associated leg of the glass insert and to form a seal between the ferrule and the capillary tube in the bore of the ferrule.

12. An easily-assembled, heat resistant connector for releasably joining end portions of at least three capillary tubes, comprising a glass insert with at least three hollow legs which are spread apart from a central portion, a main body having a cylindrical wall and an interior space inside the wall, holding means mounted on the main body and connected to the legs of the glass insert for holding the glass insert in place in said interior space and allowing passage of the end portion of the capillary tubes onto the legs of the glass insert, sealing means in the mounting means for forming a seal against the capillary tube and for forming a seal against the leg of the glass insert, and adjustment means connected to the sealing means for varying individually the strength of each seal.

* * * * *